United States Patent [19]
Allen et al.

[11] Patent Number: 6,036,672
[45] Date of Patent: Mar. 14, 2000

[54] INSTRUMENT SEAL

[75] Inventors: Donna Allen, Gurnee, Ill.; Austin R. Braganza, Milwaukee; James E. Humphreys, Jr., Genoa City, both of Wis.; John N. Johnston, Washington, N.J.

[73] Assignee: Cabot Technology Corporation, Wilmington, Del.

[21] Appl. No.: 09/076,213

[22] Filed: May 12, 1998

[51] Int. Cl.[7] .................................................. A61M 5/178
[52] U.S. Cl. ............................................ 604/167; 604/256
[58] Field of Search .................................. 604/167, 246, 604/256

[56] References Cited

U.S. PATENT DOCUMENTS

| | | |
|---|---|---|
| 4,240,411 | 12/1980 | Hosono . |
| 4,412,531 | 11/1983 | Chikashige . |
| 4,809,679 | 3/1989 | Shimonaka et al. . |
| 4,857,062 | 8/1989 | Russell . |
| 5,006,113 | 4/1991 | Fischer . |
| 5,112,321 | 5/1992 | Hiltebrandt . |
| 5,226,879 | 7/1993 | Ensminger et al. ...................... 604/93 |
| 5,290,245 | 3/1994 | Dennis . |
| 5,385,560 | 1/1995 | Wulf . |
| 5,413,561 | 5/1995 | Fischell et al. .......................... 604/167 |
| 5,437,646 | 8/1995 | Hunt et al. .............................. 604/167 |
| 5,460,615 | 10/1995 | Storz ....................................... 604/167 |
| 5,520,655 | 5/1996 | Davila et al. ............................ 604/167 |
| 5,807,350 | 9/1998 | Diaz ........................................ 604/256 |

*Primary Examiner*—Corrine McDermott
*Attorney, Agent, or Firm*—Austin R. Miller

[57] ABSTRACT

A seal is adapted for use with a suction and/or irrigation device to prevent fluid flow through a flow passage defined in the device when an instrument is inserted therethrough. The seal includes a wall traversing the flow passage. A peripheral portion of the wall occupies a plane substantially perpendicular to of the flow passage and a central portion of the wall extends away from that plane in a direction toward the device's opening. The central portion of the wall is pierceable by an instrument and the central portion is adapted for sealing contact with an external surface of the instrument upon such insertion. A seal assembly and a suction-irrigation device are also described.

28 Claims, 8 Drawing Sheets

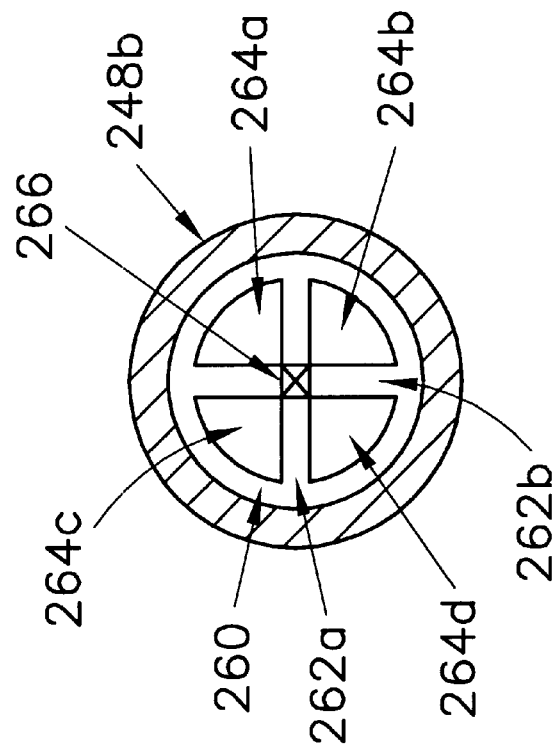
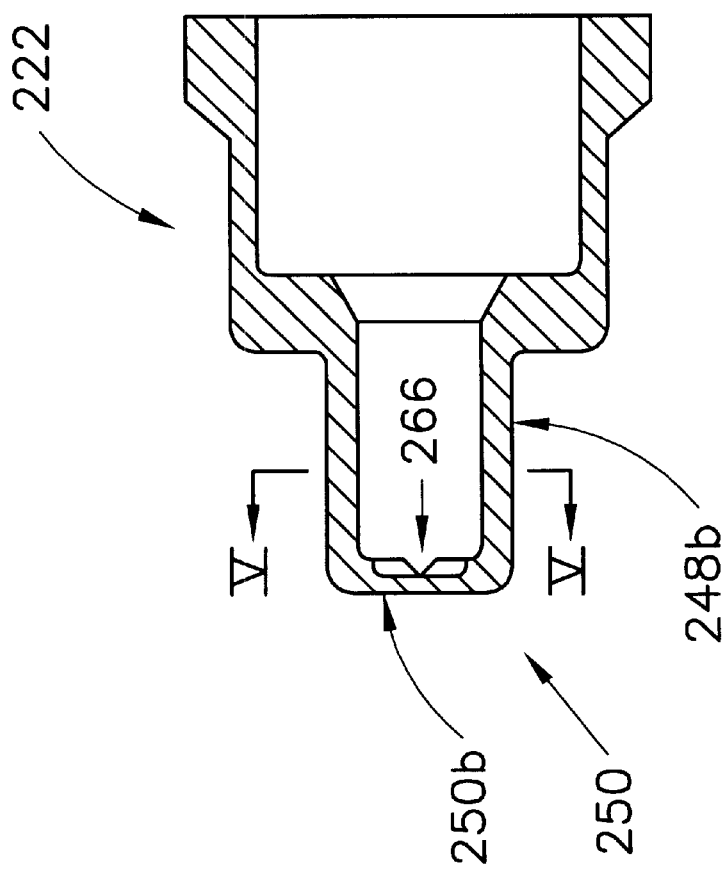

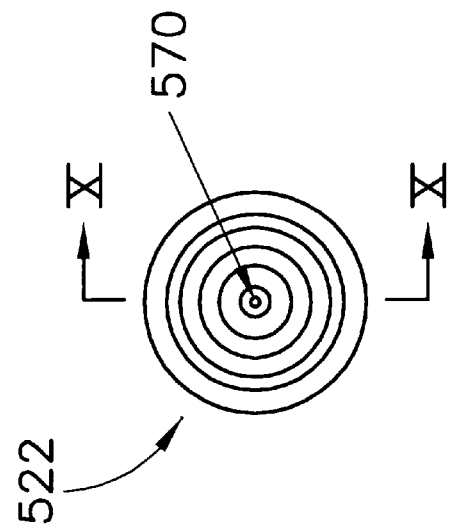
Fig. 11
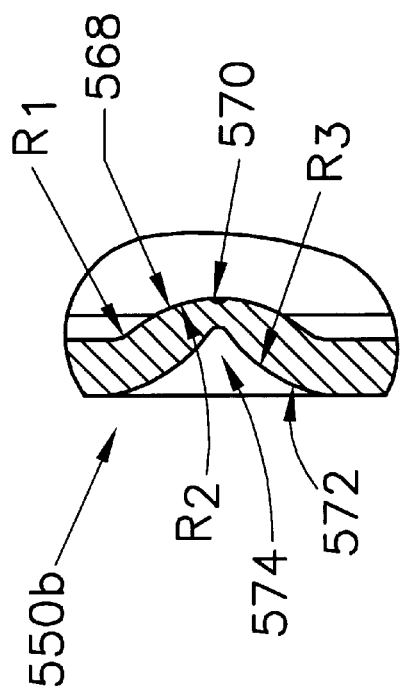
Fig. 13
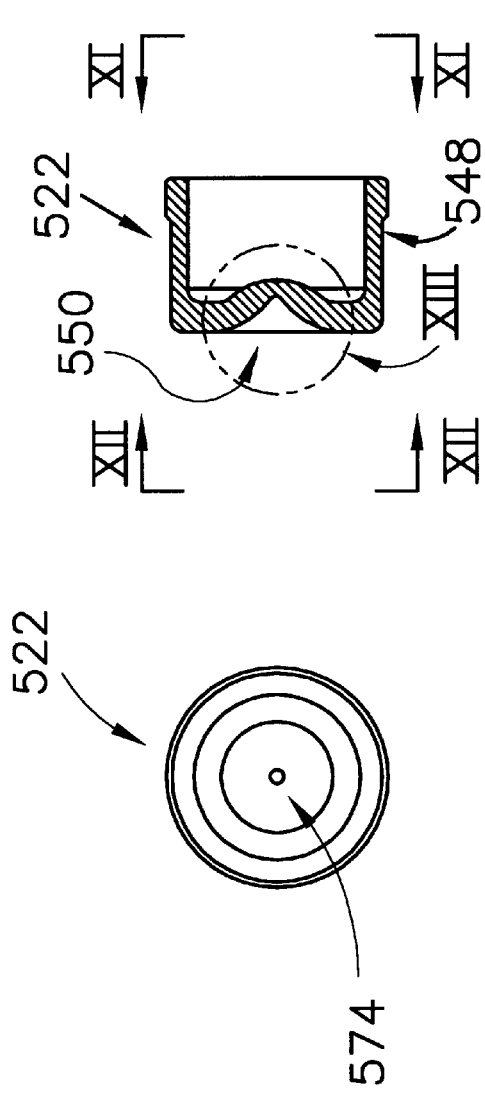
Fig. 10
Fig. 12

INSTRUMENT SEAL

BACKGROUND OF THE INVENTION

This invention provides an instrument seal adapted for use with a surgical device. In particular, the seal of this invention is well adapted for use with a suction or irrigation device, such as those often used during laparoscopic procedures, through which instruments can be inserted into the patient.

FIELD OF THE INVENTION

The rapid increase in the use of endoscopic surgical techniques has created a rising demand for improved surgical devices. Unlike traditional surgical techniques during which a surgical site is exposed by relatively large incisions, endoscopic techniques permit access to the site through one or more small openings. The surgical site, which remains substantially closed, is inflated by insufflation or pneumoperitoneum or is mechanically distended in order to allow access for the surgeon to perform a procedure.

During endoscopic procedures such as laparoscopic surgery, irrigation fluid is often delivered to the surgical site to aid visualization and to wash out the site. Irrigation fluid is subsequently removed to avoid over-accumulation. Various devices are currently available for delivering fluid into, and for suction of fluid from, a surgical site. For example, "suction-irrigation probes" are offered under the trademarks CORSON and SURGIFLEX by Circon Cabot of Racine, Wis.

Also, there is often a need during endoscopic procedures to use laser or electro-surgical or mechanical devices to vaporize, cut, cauterize or to otherwise manipulate tissue within the operative site. Such manipulation requires the insertion into the surgical site of one or more instruments such as electrode inserts, scissor inserts, retaining graspers, hydrodissection inserts, laser fiber inserts, and other instruments. These instruments preferably are provided in a variety of sizes and diameters, depending of course upon the specific procedure for which they are needed.

Many of these surgical instruments have been adapted for use in conjunction with suction-irrigation probes so that they can be inserted through an opening in the probe's body to avoid the need for an additional incision in the patient. However, the use of instruments while they are inserted into the patient through an irrigation device requires the formation of a leak-resistant and reliable seal between the inserted instrument and the irrigation device to prevent unwanted fluid leakage or loss of pressure if the surgical site is inflated. Moreover, it has been discovered that great benefit can be provided if instruments of various sizes and various diameters can be used with a single irrigation device, but such compatibility requires that the seal is capable of sealing between the irrigation device and the various instrument sizes.

OBJECTS OF THE INVENTION

It is an object of this invention to provide a seal adapted for use with a suction or irrigation device to prevent leakage around an inserted instrument.

It is a preferred object of this invention to provide a seal for use with instruments of various sizes.

Other objects of this invention will be clear in view of the following description.

SUMMARY OF THE INVENTION

A seal is provided for use with a suction or irrigation device to prevent fluid flow through a flow passage defined in the device when an instrument is inserted through it. The seal includes a wall that can be positioned adjacent to and traversing the device's flow passage in order to prevent the fluid flow. In a preferred embodiment, a peripheral portion of the wall occupies a plane that is substantially perpendicular to an axis of the flow passage, and the wall preferably includes a central portion that extends away from the perpendicular plane in a direction toward the opening through which the instrument is inserted into the device. The central portion of the wall is pierceable by the instrument and is adapted for sealing contact with an external surface of the instrument.

A seal assembly is also provided. It includes a seal, a holder for holding the seal in place with respect to the device's flow passage, and a closure for preventing fluid flow upon removal of the instrument. Preferably, the holder includes an insert, and the closure preferably includes a plug or cap.

DESCRIPTION OF THE DRAWINGS

FIG. 4 shows a cross-sectional side view of yet another embodiment of a seal according to this invention.

FIG. 5 shows a cross-sectional end view of the seal shown in FIG. 4.

FIG. 10 shows a cross-sectional side view of another embodiment of a seal according to this invention.

FIG. 11 shows a proximal end view of the seal shown in FIG. 10.

FIG. 12 shows a distal end view of the seal shown in FIG. 10.

FIG. 13 shows a cross-sectional side view of a portion of the seal shown in FIG. 10.

DETAILED DESCRIPTION OF THE INVENTION

Figure 1:
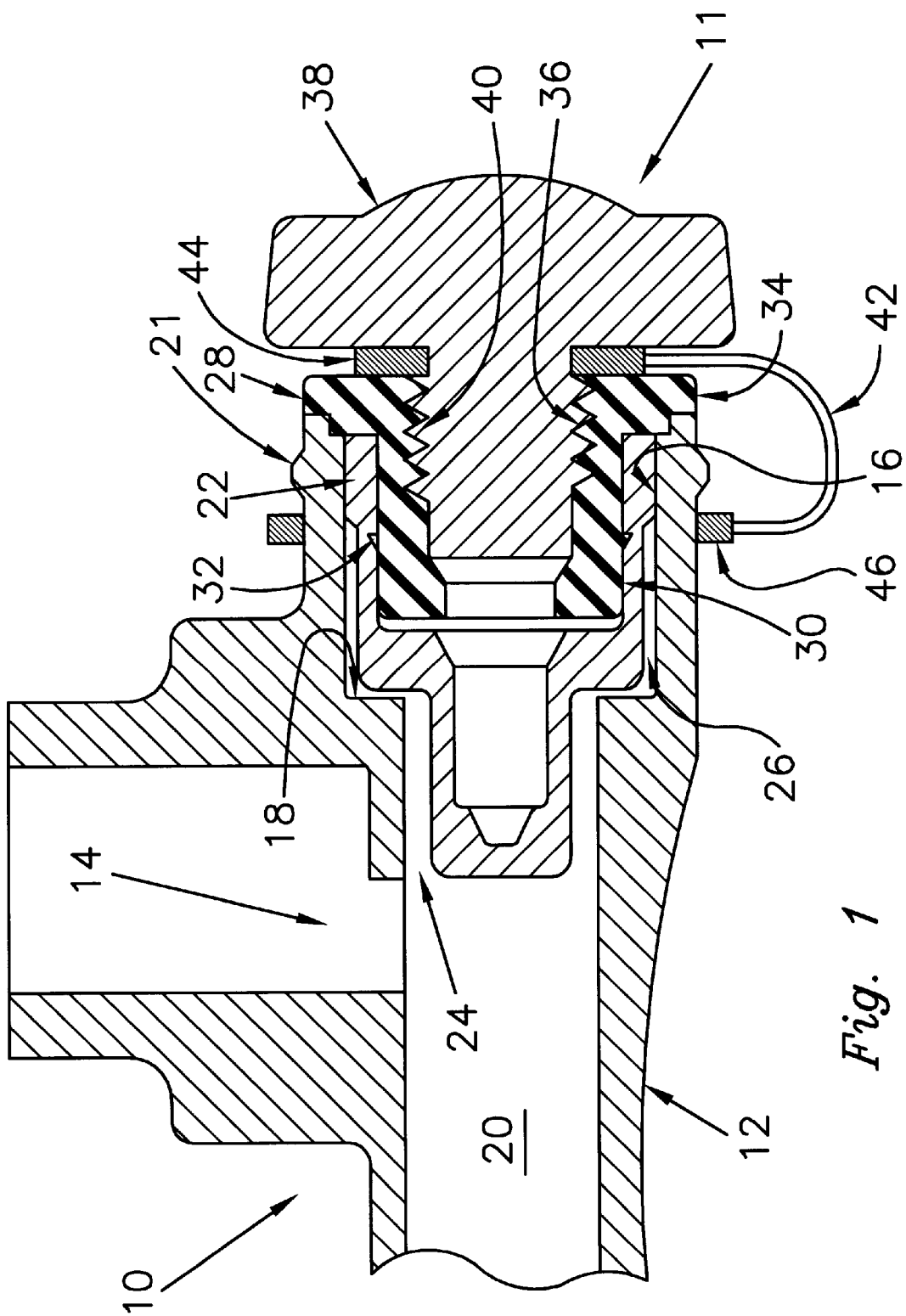
FIG. 1 shows a cross-sectional side view of a suction-irrigation probe with an embodiment of a seal assembly according to this invention.

It will be appreciated that this invention is not limited to the specific embodiments selected for illustration in the drawings and described herein. It will also be appreciated that the drawings are merely illustrative and are not necessarily to scale and that the invention is defined separately in the appended claims.

FIG. 1 illustrates a device for suction and/or irrigation utilizing an embodiment of a seal assembly according to this invention, wherein the device or probe is generally indicated by the numeral "10" and the seal assembly is generally indicated by the numeral "11". Although the embodiment of probe 10 selected for illustration is adapted for suction and/or irrigation of an operative site by removing and introducing fluid from and to the site, respectively, this invention applies equally to probes that are solely used for suction or for irrigation as well as other types of devices that could benefit from features of the invention. Unless the contrary is indicated, the term "fluid" refers to a liquid and/or gas. Also, this invention applies to devices that are intended for disposable use as well as those intended for sterilization and re-use. While probe 10 is described in the context of laparoscopic surgical procedures and related procedures, other applications or procedures are of course contemplated.

Referring to FIG. 1, probe 10 includes a probe body 12 that is preferably sized and shaped to be held within the hand of a surgeon during a medical procedure. Probe body 12 includes a valve opening 14 for suction or irrigation as well as a proximal end opening 16 at the right-hand side. Extending inwardly from opening 16 is a counterbore 18 that communicates with a flow passage 20 that extends throughout the body 12 although only the rear (proximal) portion of body 12 is illustrated. As will be described later, flow passage 20 also acts as an instrument channel through which instruments can be inserted for access to the surgical site. Although not shown, it will be understood that a probe shaft having a lumen is attachable to the distal portion of the probe body 12 for insertion into the surgical site. An inserted instrument extends though the body as well as the shaft's lumen.

Details of probe 10 are not critical to this invention. Nevertheless, additional details of suction-irrigation probes that can benefit from this invention are described in co-pending application Ser. No. 08/889,645, filed Jul. 8, 1997, and application Ser. No. 08/889,654, also filed Jul. 8, 1997, both of which are incorporated herein by reference.

Also shown in FIG. 1 is a seal assembly 11 adjacent to and extending into the proximal end portion of body 12. Seal assembly 11 includes a flexible seal 22 that is inserted into the counterbore 18 and flow passage 20 of probe body 12. Further details of seal 22 will be provided later with reference to FIG. 2 and alternative seal embodiments are illustrated in FIGS. 3–13. An annular space 24 and an annular space 26 are defined between outer surfaces of seal 22 and the inner surfaces of flow passage 20 and counterbore 18, respectively. The purpose of annular spaces 24 and 26 is to permit radial expansion of portions of seal 22 so that an instrument can be installed through the seal as will be described later.

Figure 14:
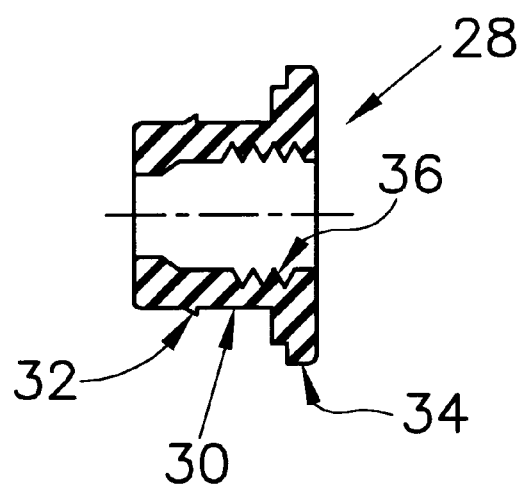
FIG. 14 shows a cross-sectional side view of an embodiment of an insert according to this invention.

Also included in seal assembly 11 is an insert 28 that is installed into the proximal end of seal 22, preferred details of which are shown in FIG. 14. Although a wide variety of materials for insert 28 are contemplated, it is preferably formed from a relatively rigid plastic material such as medical grade ABS, although other plastic or metallic materials can be substituted. Insert 28 has a substantially tubular wall 30 that extends axially into the opening 16 closely adjacent to an inner surface of seal 22. A barb ring 32 extends radially outwardly from tubular wall 30 of insert 28 in order to engage the inner surface of seal 22 so that the insert 28 cannot be unintentionally separated from seal 22. Other engaging means such as spaced barbs or ribs or beads or protrusions or grooves can be substituted for barb ring 32 and the engaging means can be provided on the seal as opposed to (or in addition to) on the insert. Also provided on insert 28 is a collar 34 to provide a surface that extends radially outwardly from tubular wall 30. In this embodiment, it engages the proximal end surface of body 12 adjacent to opening 16. Provided on an inner surface of tubular wall 30 of insert 28 are female threads 36 to engage a plug as will be described later.

Insert 28 is one possible embodiment of a holder for holding seal 22 in place with respect to flow passage 20 of body 12. Although insert 28 is illustrated as a separate component, it is also contemplated that insert 28 can be formed to be integral with or bonded to seal 22 or that the insert and seal components can otherwise be combined into a single component by design or by manufacture. Also, insert 28 can take a wide variety of forms so long as it is helpful for holding the seal 22 in place with respect to the flow passage 20.

Figure 15:
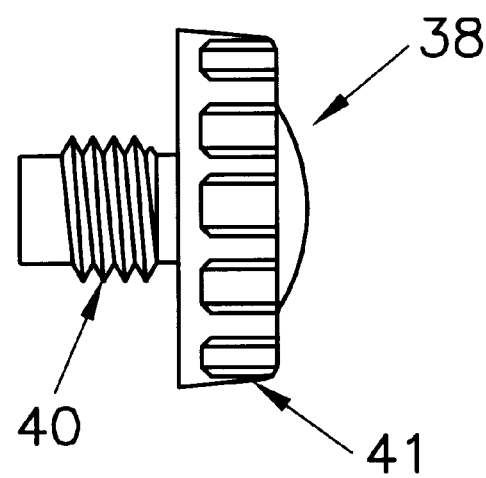
FIG. 15 shows a side view of an embodiment of a plug according to this invention.

The seal assembly 11 shown in FIG. 1 also includes a solid plug 38 having male threads 40 sized to engage the female threads 36 provided on the inner surface of insert 28. Preferred details of plug 38 are shown in FIG. 15. The purpose of plug 38 is to prevent fluid flow from flow passage 20 after an instrument has been removed from probe body 12. This feature will be clarified later with a description of the operation of the seal assembly. While plug 38 is preferred, other means for preventing fluid flow are contemplated as well, including caps, inserts and other fluid flow barriers. Plug 38 can be formed in any shape and from any plastic or metallic or other suitable material, although a relatively rigid plastic material such as high density polyethylene is preferred. Also, the means for releasable engagement between plug 38 and insert 28 can be the female threads 36 and male threads 40 shown in FIG. 1 or any other mechanism for engagement between the components. A snap-fit or interference-fit is also contemplated as is a bayonet-style connection or any other equivalent structure for releasable engagement. Also, if threads are used, the male threads can be formed on the insert and the female threads can be formed on the plug to form a cap, if desired. As shown in FIG. 15, recesses 41 are preferably formed on plug 38 to provide grasping surfaces for plug rotation. Although shown to be solid in FIG. 1, plug 38 can also be partially hollow to save material.

Figure 16:
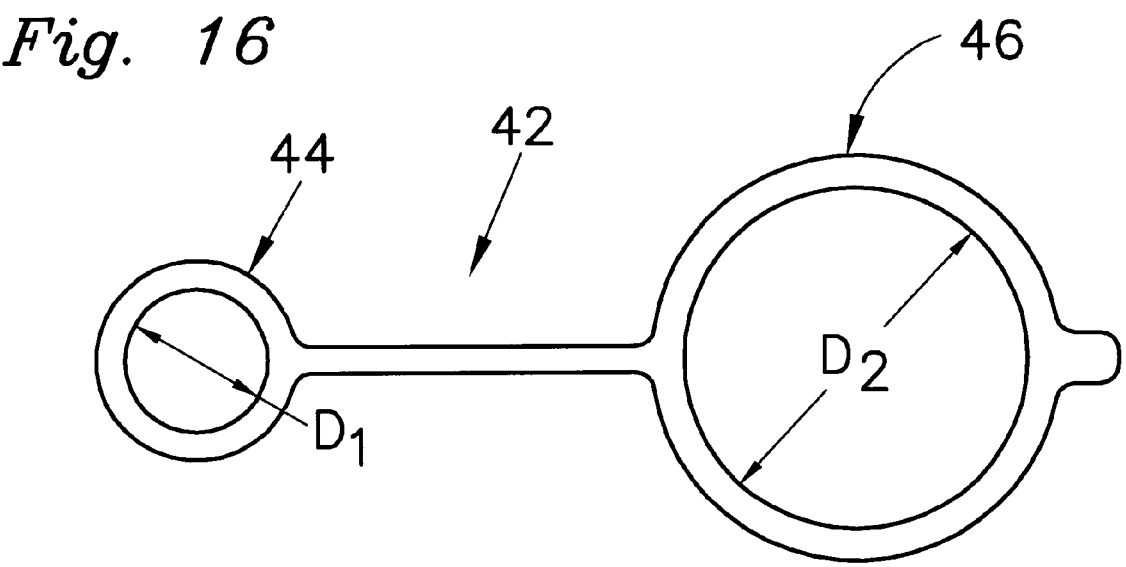
FIG. 16 shows an embodiment of a tether according to this invention.

An "umbilical cord" or tether 42 is preferably provided to connect plug 38 to probe body 12 so that plug 38 is not easily lost after it is disengaged. Preferred details are shown in FIG. 16. In one embodiment, tether 42 includes a first ring 44 at one end for engagement to plug 38. At the other end is a second ring 46 for engagement to an outer surface of probe body 12. As shown in FIG. 1, a radial bead 21 or other equivalent structure holds ring 46 in place with respect to probe body 12. Tether 42 can be formed from a wide variety of materials, including polyethylene. In any event, tether 42 can take a wide variety of forms to provide the benefit of connecting plug 38 to probe body 12 to prevent its loss.

Ring 44 has an inner diameter $D_1$ sized to fit over a portion of plug 38. Diameter $D_1$ is preferably selected so that compression of ring 44 between plug 38 and insert 28 causes sealing contact between the inner surface of ring 44 and an outer surface of plug 38. The inner diameter $D_2$ of ring 46 is preferably sized so that bead 21 can prevent its inadvertent removal.

It has been discovered that tether 42 provides another benefit in addition to preventing the plug's loss. As shown in FIG. 1, ring 44 of tether 42 is sandwiched and compressed between plug 38 and insert 28. Such compression forms a leak resistant seal that can prevent plug leakage if fluid escapes through the pierced seal and through the threads between the plug and the insert.

Figure 2:
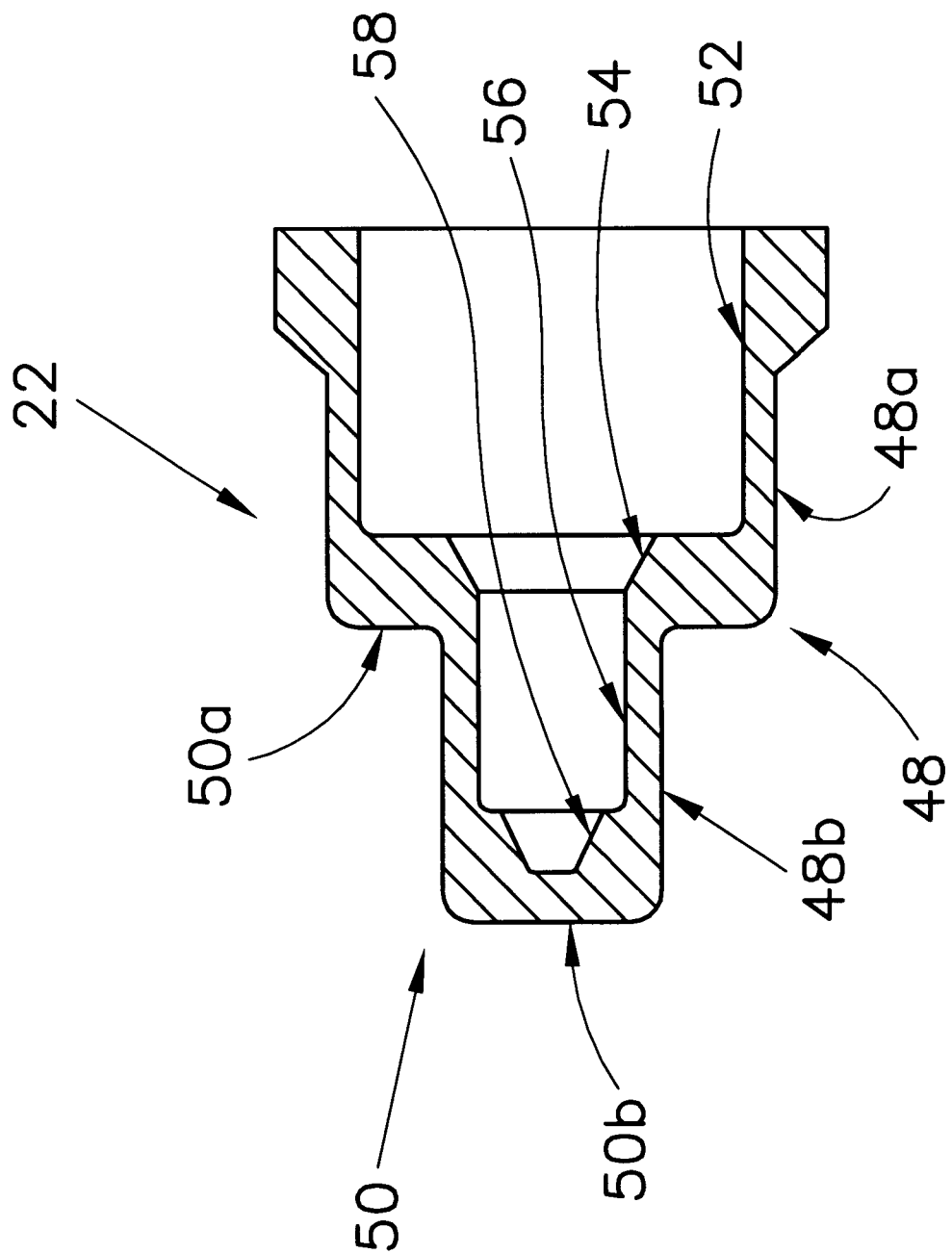
FIG. 2 shows a cross-sectional side view of an embodiment of a seal according to this invention.

Referring now to FIG. 2, one possible embodiment of seal 22 will now be described. Although a wide variety of materials can be used, seal 22 is preferably formed from an elastomeric material that is suitable for surgical use (such as silicone rubber, for example) and is most preferably provided with a durometer of about 60, shore A. Seal 22 has a perimeter or tubular wall 48 with a proximal portion 48a and a distal portion 48b. Proximal portion 48a in this embodiment preferably has a diameter that is larger than that of distal portion 48b. Seal 22 also has a wall 50 with a peripheral portion 50a and a central portion 50b. In this embodiment, central portion 50b is preferably spaced from peripheral portion 50a in the distal direction. A first counterbore 52 is formed inwardly from the proximal end of seal 22 and a taper 54 and a second counterbore 56 extend inwardly toward the distal end of the seal. A taper 58 extends into the central portion 50b of wall 50.

Seal assembly 11 is preferably provided integrally with device 10. In other words, it is preferably assembled by the manufacturer as shown in FIG. 1 and shipped to the user in a pre-assembled condition so that it is ready for use. Alternatively, seal assembly 11, or components thereof, can be provided as an accessory or as an add-on for subsequent assembly by the user into the surgical device, although not preferred.

With reference to FIGS. 1 and 2, device 10 can be used for suction and/or irrigation during an endoscopic or laparoscopic procedure with the seal, insert and plug components of seal assembly 11 in place as shown in FIG. 1. Specifically, the seal assembly 11 of seal 22, insert 28 and plug 38 permits usage of device 10 without any leakage from flow passage 20 and out through the proximal end of the device.

If it is desired to insert an instrument into the surgical site (i.e., to perform an electro-cautery procedure using an electrode, for example) plug 38 can be unthreaded from insert 28 and is permitted to dangle from body 12 by means of the tether 42. The instrument can then be inserted from the right to the left into the proximal end of device 10 through proximal opening 16. It then is advanced in the distal direction until it contacts and then pierces the central portion 50b of wall 50 and extends into flow passage 20 upon application of an insertion force from the right to the left. If the instrument is of a smaller outer diameter (perhaps 3 mm or smaller), then a seal will be formed between seal 22 and the outer surface of the instrument at the location of distal taper 58. Expansion of distal portion 48b of tubular wall 48 is permitted upon insertion of the instrument because of the provision of annular space 24 between seal 22 and the inside surface of the flow passage 20. If the instrument is of a larger outer diameter (perhaps 5 mm or larger), then a seal can be formed between seal 22 and the outer surface of the instrument at the location of proximal taper 54. The annular space 26 between seal 22 and counterbore 18 adjacent to taper 54 permits radial expansion of the seal upon insertion of the instrument.

The instrument, upon insertion, can be utilized in the usual way in the surgical site to perform any necessary procedure. At the same time, the suction and/or irrigation functions of the device 10 can be used to irrigate and evacuate the surgical site. This can be accomplished while a seal is maintained by means of sealing contact between seal 22 and an outer surface of the inserted instrument. Upon insertion, flow passage 22 and a probe shaft (not shown) act as an instrument channel and the seal acts as an instrument channel seal.

When it is later desired to remove the instrument from the rear end of device 10, the instrument can be withdrawn in the proximal direction and removed out through the proximal opening 16. The tethered plug 38 can then be threaded back into insert 28, thereby resealing the seal assembly. In other words, seal 22 may or may not be self-resealing upon removal of the instrument, and the seal need not re-seal completely to maintain the integrity of the device 10. It is the plug 38 that can be re-attached in order to prevent leakage of liquid or gaseous fluid out from the proximal end of device 10 through an opening in the seal 22 that might be left partially open for fluid flow upon removal of the surgical instrument. It is recognized that conventional seals, even those that are intended to be self-resealing, often leak upon instrument removal. The plug 38 or other closure according to this invention can be used to prevent such leakage.

Although seal 22 can be provided with a wide variety of shapes and characteristics while still achieving the benefits of this invention, it has been discovered to be especially beneficial and preferred if it is configured so that an instrument can be inserted through the seal without requiring an excessive insertion force. Most preferably, a 3 mm instrument such as a ball electrode is insertable with an insertion force not exceeding about six pounds. Larger diameter instruments would be expected to require a greater insertion force. Also, it is preferable if the seal can withstand fluid leakage around the outer surface of the instrument even when the pressure within the irrigation device rises during use for an extended period of time. Most preferably, the seal can withstand such leakage as the pressure approaches about 500 mm Hg or more for a duration of about one hour. Furthermore, it is preferred that the seal is capable of sealing around the outer surfaces of instruments of various diameters. Most preferably, the same seal configuration prevents leakage around instruments as small as about 3 mm in diameter or even smaller and as large as about 5 mm in diameter or even larger.

FIGS. 3–13 illustrate alternative embodiments of a seal according to this invention. It should be noted that other seal embodiments are contemplated as well for use in a seal assembly such as seal assembly 11 shown in FIG. 1.

Figure 3:
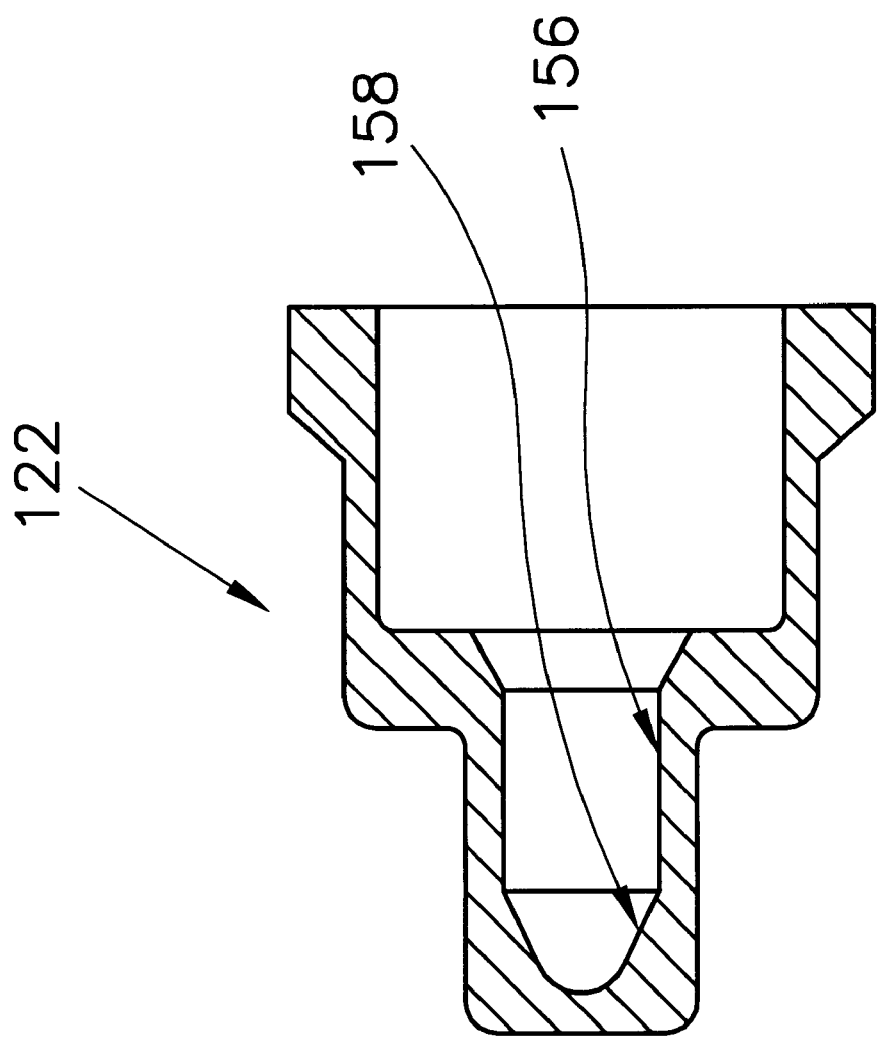
FIG. 3 shows a cross-sectional side view of another embodiment of a seal according to this invention.

FIG. 3 illustrates a seal 122 that is similar to seal 22 shown in FIG. 2. The most significant difference is that seal 122 includes a second counterbore 156 that transitions directly into a taper 158. In contrast, seal 22 has a shoulder between second counterbore 56 and distal taper 58.

The seal embodiment designated by the numeral "222" in FIGS. 4 and 5 is similar to seals 22 and 122 except for the configuration of the central portion of its distal wall. Specifically, central portion 250b of the seal's wall 250 is configured to improve the performance of the seal as an instrument is inserted to pierce central portion 250b and to create a reliable seal with the outer surface of the instrument. Referring specifically to FIG. 5, central portion 250b has a shoulder 260 adjacent to distal portion 248b of the tubular wall as well as perpendicularly arranged ribs 262a and 262b that extend inwardly from shoulder 260. Shoulder 260 and ribs 262a and 262b together define four recesses 264a, 264b, 264c, and 264d. At the intersection of ribs 262a and 262b is provided a pointed recess 266 which is also visible in FIG. 4. A sharp point at the base of pointed recess 266 acts to center central portion 250b with respect to the tip of an inserted instrument and to initiate the piercing of central portion 250b of seal 222 as an inserting force is applied to the instrument.

FIGS. 6–9 illustrate yet another seal embodiment. Here, a seal 322 is similar to the others except that it only includes a single taper 358. Also, as is most clearly illustrated in FIG. 7, a central portion 350b of the seal's wall 350 is provided with a structure that is adapted to center an instrument as it is inserted into seal 322 and to initiate the piercing of central portion 350b.

Figure 7:
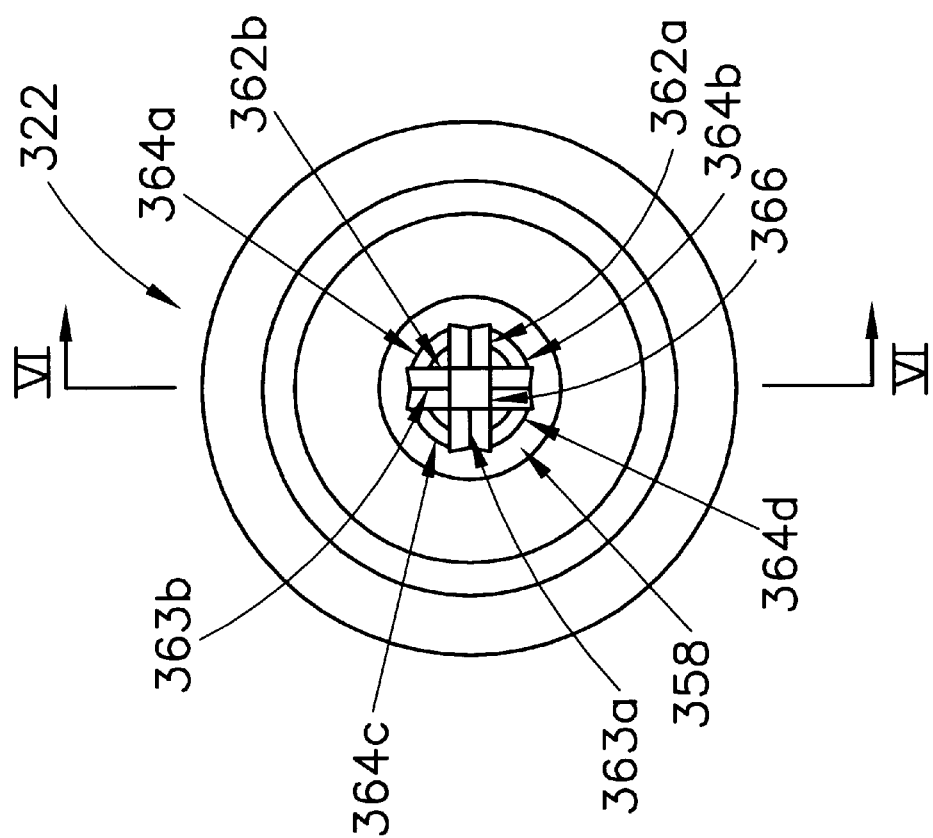
FIG. 7 shows a proximal end view of the seal shown in FIG. 6.
Figure 6:
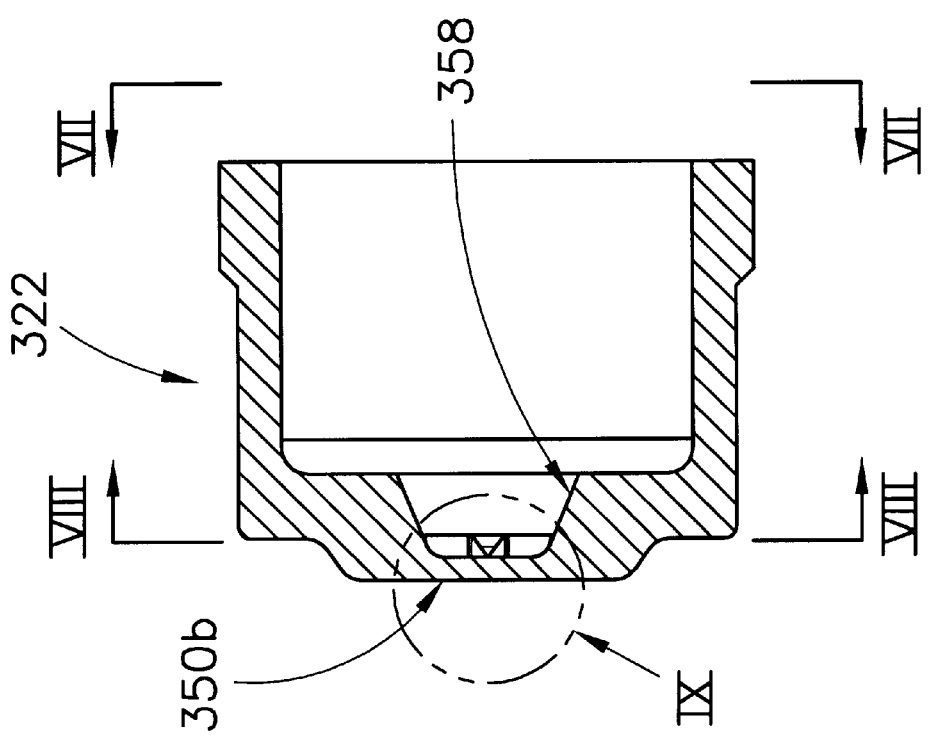
FIG. 6 shows a cross-sectional side view of still another embodiment of a seal according to this invention.
Figure 9:
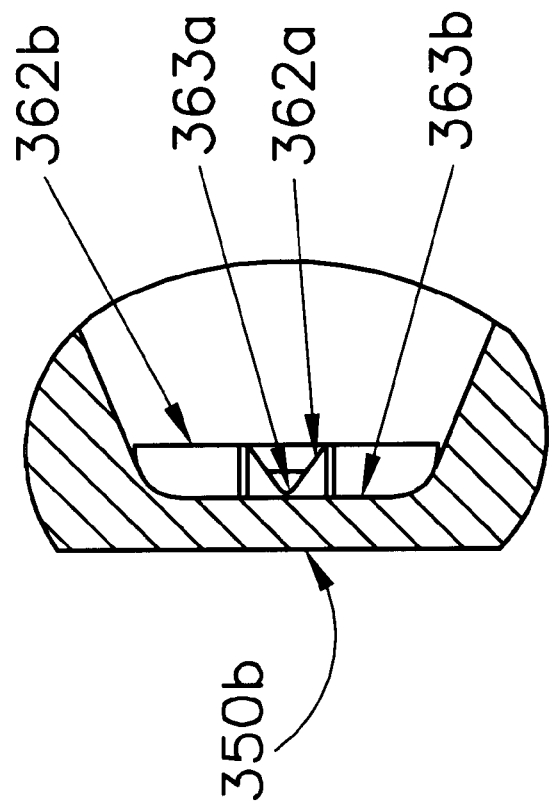
FIG. 9 shows a cross-sectional side view of a portion of the seal shown in FIG. 6.
Figure 8:
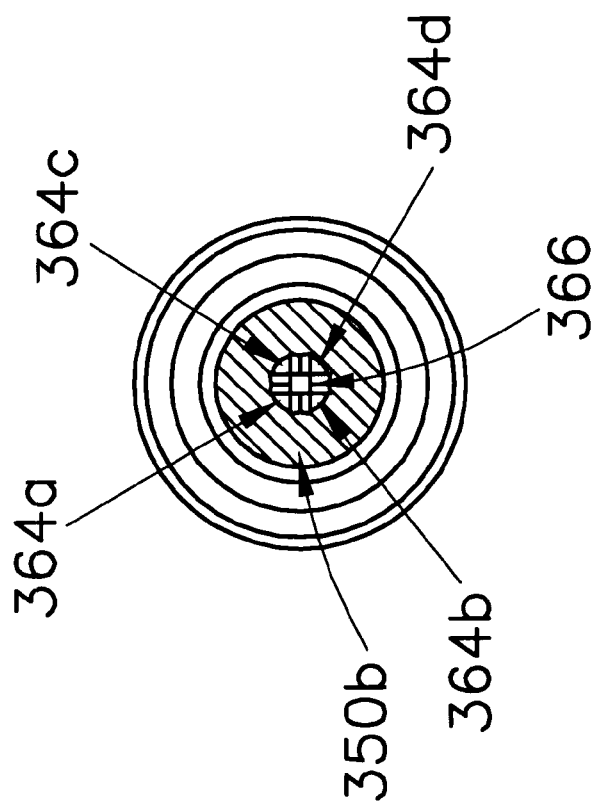
FIG. 8 shows a cross-sectional end view of the seal shown in FIG. 6.

Referring specifically to FIGS. 7–9, seal 322 has at its central wall portion 350b two perpendicularly arranged ribs 362a and 362b. These ribs are like ribs 262a and 262b of seal 222 except that they include longitudinally extending valleys 363a and 363b at or near their centers. Ribs 362a and 362b meet at the center of wall 350 to define a square recess 366 that has a substantially flat bottom. Ribs 362a and 362b also define four recesses 364a, 364b, 364c, and 364d. These contours at wall portion 350b facilitate penetration of an instrument through the seal and provide reliable sealing contact around the instrument upon its insertion.

The seal embodiment 522 shown in FIGS. 10–13 has been discovered to have especially beneficial performance. It differs from the others in that it at least partially eliminates the tapered regions such as taper 54 and taper 58 of seal 22. Instead, it includes a substantially straight tubular wall 548 and a distal wall 550, the outer peripheral edges of which share a plane that is substantially perpendicular to the axis of flow passage 20 when seal 522 is installed in the device. Also, a central portion 550b of wall 550 extends away from the perpendicular plane in the proximal direction.

It has been discovered that significant performance benefits result from seal contours such as the preferred contours illustrated in FIG. 13. At the central portion 550b of wall 550, it can be seen that a portion of wall 550 extends in the proximal direction and into an interior region defined by tubular wall 548 and wall 550. When installed in an irrigation device such as device 10, central portion 550b extends toward the proximal opening 16.

As is best illustrated in FIG. 13, central portion 550b of wall 550 has a proximal surface 568 that curves away from the perimeter portion of wall 550 along a first radius $R_1$ and then curves in the opposite direction back towards the center of wall 550 along a second radius $R_2$. At the center of wall 550, proximal surface 568 defines a cup-shaped recess 570 that extends into the wall. Central portion 550b also has a distal surface 572 that curves from the peripheral portion of wall 550 along a third radius $R_3$. Such curvature defines a substantially conical recess 574 that extends into the wall 550. As shown in FIG. 13, the plane in which the center of wall 550 exists is shifted in the proximal direction from the plane occupied by the peripheral region of the wall.

In use, a surgical instrument is installed through the back proximal end of device 10 so that it contacts seal 522 from the right in FIG. 10. The instrument will then pierce wall 550 of seal 522 at or about recess 570 and push central portion 550b to the left in the distal direction upon application of the requisite insertion force. A seal is then formed around the outer surface of the instrument to prevent fluid flow past wall 550. Depending of course upon the relative dimensions and materials of the seal as well as the size of the instrument, central portion 550b of seal 522 is likely to relax and move together with the instrument slightly to the right in the proximal direction so that the seal is primarily formed between the outer surface of the instrument and the distal surface 572 of seal 522 at a location adjacent to or at recess 574. The dimensions and material of seal 522 are preferably selected to bring about such a seal and are most preferably selected to bring about a seal around instruments of various sizes.

Sample seals corresponding to the embodiment shown in FIGS. 10–13 and formed from silicone rubber were tested before and after insertion of various 3 mm and 5 mm instruments, as summarized here:

| Sample No. | Inserted Instrument (Circon Cabot Part No.) | Leak Rate (L/min at 500 mm Hg) | Instrument Insertion Force ($lb_f$) | Instrument Withdrawal Force ($lb_f$) |
|---|---|---|---|---|
| 1 | 5 mm Strong | 0 | 10.5 | 2.7 |
| 2 | Forceps | 0 | 9.7 | 5.9 |
| 3 | (006811-901) | 0 | 12.0 | 5.2 |
| 4 |  | 0 | 9.5 | 2.8 |
| 5 |  | 0 | 9.8 | 3.6 |
| 6 |  | 0 | 11.6 | 2.3 |
| 7 | 3 mm J-hook | 0 | 6.3 | 4.3 |
| 8 | Electrode (006124-901) | 0 | 13.2 | 3.2 |

Significantly, non of the samples leaked at pressures up to at least about 500 mm Hg before of after instrument insertion through the seals. The average 5 mm instrument insertion force was about 10.52 $lb_f$ in order to pierce the seal and advance the instrument through it. The average 3 mm instrument insertion force was lower at about 9.75 $lb_f$, as expected, but the high insertion force value for Sample No. 8 is believed to be the result of off-center contact between the tip of the 3 mm J-hook electrode and the seal's wall. The average withdrawal force was much lower than the insertion force, as expected, at about 3.75 $lb_f$ for both the 5 mm instrument and the 3 mm instrument.

Accordingly, the tests confirmed that the seal accomplishes the preferred benefits of the invention; namely, it seals against fluid flow prior to instrument insertion to prevent leakage, exhibits a favorable instrument insertion force, seals against the surface of an inserted instrument to prevent leakage, permits instrument withdrawal with ease, and can be re-sealed upon instrument removal. The tests also confirmed that the seal can be used with instruments having a range of sizes and shapes.

It will be understood that many variations and modifications of the specific embodiments selected for illustration in the Figures can be made without departing from the spirit or scope of this invention. The specific materials and dimensions recited herein for the purpose of illustration can be changed without forfeiting the benefits of the invention.

It will be appreciated that the components of the seal assembly described herein can be substituted with equivalent components that accomplish substantially the same function: the seal embodiments illustrated herein can be substituted with any structure that can form a flow-resistant seal at an inserted instrument; the insert embodiments can be substituted with any structure that can help to hold the seal in place with respect to a flow passage; and the plug embodiments can be substituted with any structure that can help to prevent fluid flow upon removal of an inserted instrument.

Also, two or more of the seal assembly components can be combined into one. For example, the seal component and the insert component can be substituted with a single component that can seal at an inserted instrument while remaining in place with respect to the flow passage, and the insert component and the plug component can be substituted with a single component that can help hold a seal in place and prevent fluid flow upon removal of an inserted instrument. Also, the seal according to this invention can consist of a single component that can seal an inserted instrument, remain in place with respect to the flow passage, and reseal itself to prevent fluid flow upon removal of the inserted instrument.

Other variations can be made without departing from the scope of the invention, which is defined separately in the following claims.

What is claimed is:

1. A device adapted for suction and/or irrigation of a medical site and providing for insertion of a medical instrument through a probe having a suction and irrigation flow passage and an operative passageway for insertion of a surgical instrument through said flow passage for conducting said medical procedure, said device comprising:

a body having an inner surface defining said flow passage and an opening for access of suction and irrigation media to said flow passage, said flow passage also being sized to accommodate a medical instrument, having an exterior surface, therethrough;

a seal comprising a body having an interior region extending into said flow passage and having a wall having a central portion and a peripheral portion, wherein said peripheral portion of said wall substantially perpendicularly traverses said flow passage, said central portion of said wall extends from said peripheral portion, said wall being pierceable by said medical instrument as said instrument is inserted into and through said flow passage, said wall being adapted for sealing contact with said external surface of said instrument upon its insertion through said wall to prevent said fluid flow, said seal further comprising a proximal surface defining said interior region;

a holder, having an inner surface and an outer surface, connected to hold said seal in place with respect to said flow passage, said holder having a distal portion extending into said interior region of said seal, and having a closure contact portion; and a closure attached to said body to prevent fluid flow through said opening of said body upon removal of said medical instrument from said opening, said closure having a surface positioned for contact with said closure contact portion of said holder.

2. The device defined in claim 1, wherein said central portion of said wall of said seal extends into said interior region defined by said seal.

3. The device defined in claim 1, wherein said central portion of said wall of said seal comprises a distal surface that defines a recess extending into said wall.

4. The device defined in claim 1, wherein said central portion of said wall of said seal comprises a proximal surface that extends toward said opening in said device.

5. The device defined in claim 4, wherein said proximal surface of said central portion defines a recess extending into said wall.

6. A seal adapted for use with a suction and/or irrigation device to prevent fluid flow through a flow passage, defined by an inner surface of said device, when an instrument having an exterior surface is inserted into an opening defined in said device and through said flow passage, said seal comprising:

a wall, having a central portion and a peripheral portion, said wall positionable adjacent to said inner surface of said device, said peripheral portion of said wall substantially perpendicularly traverses said flow passage and said central portion of said wall extends away from said peripheral portion of said wall in a proximal direction towards said opening;

said central portion of said wall being pierceable by said instrument as said instrument is inserted through said opening and said flow passage, and wherein said central portion of said wall is adapted for sealing contact with said external surface of said instrument upon insertion to prevent said fluid flow; said seal defining an interior region into which said central portion of said wall extends.

7. The seal defined in claim 6, wherein said central portion of said wall is adapted for sealing contact with external surfaces of instruments having various sizes.

8. The seal defined in claim 6, wherein said central portion of said wall is adapted for sealing contact with an external surface of an instrument having an outer diameter from about 3 mm to about 5 mm.

9. The seal defined in claim 6, said central portion of said wall comprising a distal surface that defines a recess extending into said wall.

10. The seal defined in claim 6, said central portion of said wall comprising a proximal surface that extends toward said opening in said device.

11. The seal defined in claim 10, wherein said proximal surface of said central portion defines a recess extending into said wall.

12. The seal defined in claim 6, further comprising a holder positioned to contact a portion of said seal and hold said seal in place with respect to said flow passage of said device.

13. The seal defined in claim 12, wherein said holder comprises an insert capable of engaging said opening in said device.

14. A seal adapted for use with a suction and/or irrigation device to prevent fluid flow through a flow passage, defined by an inner surface of said device, when an instrument having an exterior surface is inserted into an opening defined in said device and through said flow passage, said seal comprising:

a wall, having a central portion and a peripheral portion, said wall positionable adjacent to said inner surface of said device, said peripheral portion of said wall substantially perpendicularly traverses said flow passage, said central portion of said wall extends away from said peripheral portion of said wall in a proximal direction towards said opening;

said central portion of said wall being pierceable by said instrument as said instrument is inserted through said opening and said flow passage, and wherein said central portion of said wall is adapted for sealing contact with said external surface of said instrument upon insertion to prevent said fluid flow;

said seal further comprising a holder positioned to contact a portion of said seal and hold said seal in place with respect to said flow passage of said device;

said seal further comprising a closure capable of removably engaging said holder for preventing said fluid flow through said opening of said device upon removal of said instrument from said opening.

15. The seal defined in claim 14, wherein said closure comprises a plug or cap positionable adjacent to said opening in said device.

16. A seal assembly for use with a surgical device having a body with an inner surface defining a flow passage, said body having an opening for access to said flow passage, said opening of said body and said flow passage being sized to accommodate an instrument, having an exterior surface, when inserted therethrough, said seal assembly comprising:

a seal comprising a wall defining an interior region of said seal having a central portion and a peripheral portion, said peripheral portion of said wall substantially perpendicularly traverses said flow passage, said central portion of said wall extends from said peripheral portion said wall being pierceable by an instrument having an exterior surface, said wall being adapted for sealing contact with said external surface of said instrument upon insertion through said wall to prevent said fluid flow;

a holder, having an inner surface and an outer surface, to secure said seal with respect to said flow passage, said holder comprising a distal portion extending into said interior region of said seal, and a closure contact surface; and a closure adapted to prevent fluid flow through said opening of said body upon removal of said instrument from said opening, said closure removably engages said holder.

17. The seal assembly defined in claim 16, wherein said wall of said seal is adapted for forming a sealing contact with external surfaces of instruments having various sizes.

18. The seal assembly defined in claim 16, wherein said wall is adapted for forming a sealing contact with an external surface of an instrument having an outer diameter from about 3 mm to about 5 mm.

19. The seal assembly defined in claim 16, further comprising a fastener for engaging said outer surface of said holder with respect to said interior region of said seal.

20. The seal assembly defined in claim 16, wherein said holder comprises a radially extending surface for contact adjacent to said opening of said device.

21. The seal assembly defined in claim 16, further comprising means for releasable engagement between said holder and said closure.

22. The seal assembly defined in claim 21, wherein said releasable engagement means comprises threads formed on said holder and mating threads formed on said outer surface of said closure.

23. The seal assembly defined in claim 16, further comprising a tether connected between said closure and said device.

24. The seal assembly defined in claim 16, wherein said peripheral portion of said wall substantially perpendicularly traverses said flow passage, said wall further comprising a central portion that extends away from said peripheral portion of said wall in a proximal direction toward said opening in said device through which said instrument is inserted.

25. The seal assembly defined in claim 24, wherein said central portion extends into said interior region defined by said seal.

26. The seal assembly defined in claim 24, wherein said central portion of said wall of said seal comprises a distal surface that defines a recess extending into said wall.

27. The seal assembly defined in claim 24, wherein said central portion of said wall of said seal comprises a proximal surface that extends toward said opening in said device.

28. The seal assembly defined in claim 27, wherein said proximal surface of said central portion defines a recess extending into said wall.

* * * * *